United States Patent
Leveque et al.

(10) Patent No.: US 8,351,041 B2
(45) Date of Patent: Jan. 8, 2013

(54) METHOD OF OBSERVING BIOLOGICAL TISSUE, IN PARTICULAR HUMAN SKIN

(75) Inventors: Jean-Luc Leveque, Paris (FR); Neso Sojic, Cestas (FR)

(73) Assignee: L'Oreal, Paris (FR)

( * ) Notice: Subject to any disclaimer, the term of this patent is extended or adjusted under 35 U.S.C. 154(b) by 1435 days.

(21) Appl. No.: 11/666,912

(22) PCT Filed: Nov. 28, 2005

(86) PCT No.: PCT/IB2005/053927
§ 371 (c)(1),
(2), (4) Date: Oct. 12, 2007

(87) PCT Pub. No.: WO2006/056965
PCT Pub. Date: Jun. 1, 2006

(65) Prior Publication Data
US 2008/0186496 A1    Aug. 7, 2008

Related U.S. Application Data

(60) Provisional application No. 60/647,764, filed on Jan. 31, 2005.

(30) Foreign Application Priority Data

Nov. 26, 2004    (FR) ...................................... 04 12581

(51) Int. Cl.
*G01N 21/55* (2006.01)
(52) U.S. Cl. .................... 356/445; 606/4; 606/9; 601/3; 601/15; 600/407; 600/476; 607/88; 348/77; 378/62; 378/63

(58) Field of Classification Search ................... 607/94; 378/37, 62, 63; 606/9, 4; 356/419, 445; 385/34; 601/3, 15
See application file for complete search history.

(56) References Cited

U.S. PATENT DOCUMENTS

| | | | |
|---|---|---|---|
| 5,893,364 | A | 4/1999 | Haar et al. |
| 6,111,653 | A | 8/2000 | Bucknell et al. |
| 6,175,678 | B1 | 1/2001 | Sanghera et al. |
| 6,177,984 | B1 | 1/2001 | Jacques |
| 6,411,838 | B1 | 6/2002 | Nordstrom et al. |

(Continued)

FOREIGN PATENT DOCUMENTS

JP    U-01-117756    8/1989

(Continued)

OTHER PUBLICATIONS

Japanese First, Second and Final Office Actions issued in Japanese Application No. 2002-190173.

(Continued)

*Primary Examiner* — Tse Chen
*Assistant Examiner* — Baisakhi Roy
(74) *Attorney, Agent, or Firm* — Oliff & Berridge, PLC (57) ABSTRACT

The present invention relates to a method of observing biological tissue, the method comprising: collecting through a first end of a bundle of optical fibers light from a surface of the tissue; observing at least one image of the tissue at a second end of the bundle, while injecting light into the second end of the bundle to illuminate the surface of the tissue.

67 Claims, 4 Drawing Sheets

U.S. PATENT DOCUMENTS

| | | | |
|---|---|---|---|
| 6,741,884 B1 | 5/2004 | Freeman et al. | |
| 6,975,898 B2 | 12/2005 | Seibel | |
| 7,322,972 B2 * | 1/2008 | Viator et al. | 606/9 |
| 7,742,561 B2 * | 6/2010 | Ueki | 378/63 |
| 8,026,942 B2 * | 9/2011 | Payonk et al. | 348/77 |
| 8,027,709 B2 | 9/2011 | Arnone et al. | |
| 2003/0202630 A1 * | 10/2003 | Chen | 378/62 |
| 2003/0227628 A1 * | 12/2003 | Kreimer et al. | 356/419 |
| 2004/0028329 A1 * | 2/2004 | Reed et al. | 385/34 |
| 2004/0042013 A1 | 3/2004 | Querleux et al. | |
| 2004/0125996 A1 | 7/2004 | Eddowes et al. | |
| 2005/0177208 A1 * | 8/2005 | Irwin | 607/94 |
| 2006/0004306 A1 * | 1/2006 | Altshuler et al. | 601/3 |
| 2006/0004347 A1 * | 1/2006 | Altshuler et al. | 606/4 |
| 2006/0020309 A1 * | 1/2006 | Altshuler et al. | 607/88 |
| 2006/0058712 A1 * | 3/2006 | Altshuler et al. | 601/15 |
| 2006/0092315 A1 * | 5/2006 | Payonk et al. | 348/370 |
| 2008/0186496 A1 * | 8/2008 | Leveque et al. | 356/445 |
| 2010/0145321 A1 * | 6/2010 | Altshuler et al. | 606/9 |

FOREIGN PATENT DOCUMENTS

| | | |
|---|---|---|
| JP | A-06-095996 | 4/1994 |
| JP | A-07-019839 | 1/1995 |
| JP | A-07-071945 | 3/1995 |
| JP | A-07-143967 | 6/1995 |
| JP | A-07-323013 | 12/1995 |
| JP | A-09-511237 | 11/1997 |
| JP | A-10-127586 | 5/1998 |
| JP | A-10-333057 | 12/1998 |
| JP | A-11-064160 | 3/1999 |
| JP | A-11-183371 | 7/1999 |
| JP | 11-267105 | 10/1999 |
| JP | U-3065205 | 2/2000 |
| JP | A-2000-186998 | 7/2000 |
| JP | A-2001-070251 | 3/2001 |
| JP | A-2001-166219 | 6/2001 |
| JP | A-2003-505130 | 2/2003 |
| JP | A-2003-199727 | 7/2003 |
| JP | A-2003-535659 | 12/2003 |
| WO | WO 95/24888 A1 | 9/1995 |
| WO | WO 02/069784 A2 | 9/2002 |
| WO | WO 2004/026125 A1 | 4/2004 |
| WO | WO 2004/043255 A1 | 5/2004 |

OTHER PUBLICATIONS

Communication from European Patent Office issued in Application No. EP 08 807 215.8; May 10, 2010.

Dec. 28, 2009 Office Action issued in European Patent Application No. 05807215.8.

Sep. 4, 2012 Office Action issued in Japanese Application No. 2007-542488 (with partial translation).

* cited by examiner

METHOD OF OBSERVING BIOLOGICAL TISSUE, IN PARTICULAR HUMAN SKIN

The present invention relates to observing biological tissue, and more particularly, but not exclusively, to observing human skin.

It has been known for many years that the size of corneocytes at the surface of the skin is directly related to their transit speed in the epidermis.

In young individuals, the cells are small because the level of metabolism in the epidermis is high and the transit time is short. The opposite applies in old people.

Measuring the size of corneocytes can therefore provide useful information, in particular for cosmetics.

Currently, this measurement can be carried out ex vivo, with the cells being collected by scraping or by exposing the skin to a detergent solution, and then being dyed and placed under a microscope. Their size is determined by image processing, with at least one thousand cells preferably being used in order to determine the mean size with accuracy.

There exists another possibility whereby an adhesive is applied to the skin, said adhesive taking the surface cells with it when removed. The surface cells are dyed, and then measured under a microscope.

In vivo, the corneocytes are observed by means of a confocal microscope, after the skin has been dyed.

A confocal microscope is an instrument that is costly and complex to use, and in addition, the number of corneocytes present in the observed field is relative small, thereby requiring numerous regions to be observed in order to determine the mean size of the corneocytes.

The invention seeks to propose a novel means of enabling corneocytes to be observed, for example in vivo.

In one of its aspects, the invention provides a method of observing biological tissue, the method comprising:
collecting through a first end of a bundle of optical fibers light from a surface of the tissue;
observing at least one image of the tissue at a second end of the bundle, while injecting light into the second end of the bundle to illuminate the surface of the tissue.

In exemplary embodiments, the first end of the bundle of optical fibers is oriented in a direction substantially perpendicular to the surface of the tissue.

The first end of the bundle may be put into contact with the surface of the tissue.

In a variant, the first end of the bundle may be spaced from the surface of the tissue by a distance.

The invention may be configured to obtain an image of the surface of the tissue that can be useful, e.g. for skin, for determining the mean size of corneocytes, without any need for complex equipment, such as a confocal microscope.

Light may be collected by the first end of the bundle through an optical system comprising at least one lens.

The use of such an optical system may make it possible to increase the spatial resolution and to minimize a pixelisation effect.

In exemplary embodiments, the distance between the optical system and the surface of the tissue may range from 100 µm to 1 mm, for example may range from 200 µm to 500 µm.

The at least one lens of the optical system may comprise a magnifying lens and/or a collecting lens.

The optical system may comprise a first lens and second lens, light from the surface of the tissue passing through the second lens and then the first lens. The first lens may be a collimating lens and the second lens may be magnifying lens.

In exemplary embodiments, the length of the first lens may range from 4.4 to 6.8 mm. The length of the second lens may range from 1.8 to 2.9 mm.

The at least one lens of the optical system may comprise a lens with an index gradient. This lens may have a g value of the index gradient at 670 nm greater than or equal to 0.25 $mm^{-1}$.

The at least one lens of the optical system may be cylindrical and may have an external diameter less than or equal to 2 mm. Both the first and second lens may be cylindrical.

The size of the fibers used determines the resolution of the image. The spatial resolution may be better than 5 micrometers (µm), preferably better than 4 µm, and more preferably better than 3 µm. The optical fibers may present a diameter that is less than or equal to 4 µm, better less than or equal to 3 µm, e.g. that lies in the range from about 2 µm to about 3 µm.

Using an optical system as defined above may provide a resolution better than 2 µm, or even better than 1.5 µm.

The relative positions of the fibers within the bundle may be the same at the inlet and at the outlet of said bundle. Each fiber may correspond to one pixel of the image.

The number of optical fibers in the bundle may be greater than or equal to 2500, being preferably greater than or equal to 5000. The number of optical fibers in the bundle may thus be greater than or equal to 7500, and better greater than or equal to 10,000.

The section occupied by the bundle of optical fibers may be greater than or equal to 0.01 square millimeters ($mm^2$), better greater than or equal to 0.05 $mm^2$, better still greater than or equal to 0.07 $mm^2$, e.g. greater than or equal to 0.1 $mm^2$, or even several tenths of a $mm^2$ or greater, e.g. 1 $mm^2$ or several $mm^2$.

The tissue may be natural or artificial tissue, for example skin or hair. The observation may be an in vivo or an in vitro observation.

The method may include image processing so as to determine information associated with corneocytes, said information relating to the number of corneocytes present in the image and/or to their mean or median size, for example.

Prior to making the observation, a fluorescent marker may be put into contact with the tissue.

In the presence of the fluorescent marker, light centered on a first wavelength may be injected into the fibers, and the observation may be made at a second wavelength that is different from the first. By way of example, the wavelengths may be selected as a function of the fluorescent marker, so as to maximize contrast in the obtained image.

The image may be acquired with an array sensor, for example a CCD sensor.

At least two observations may be made at two different locations of the tissue. Two observations may be made at two respective regions that have been exposed in different ways to a given environment, e.g. two regions that have been exposed in different ways to ultraviolet light and/or two regions that have been treated differently with at least one substance. A plurality of observations may be made at different locations, and the results of the various observations may be processed statistically to obtain a value that is representative of an observed parameter, for example a mean or median value.

Information relating to aging of the skin may be delivered as a function of the number of observed corneocytes and/or as a function of their mean or median size, for example.

The observed surface may be situated outside or inside a hair follicle.

The result of an observation may be compared with reference data, which may come from the observed person or from a reference population.

By way of example, it is possible to compare information resulting from an observation made during a first time interval with information resulting from an observation made during a second time interval that is different from the first. By way of example, this can make it possible to establish a diagnosis or a prognosis, or to determine the effect of a substance or of a treatment.

In another of its aspects, the invention also provides a method of revealing the effect of a treatment, for example a non-therapeutic treatment, the method comprising:
  before the treatment, making a first observation by means of the method as defined above;
  after the treatment, making a second observation by means of the same method; and
  comparing the results of the first and second observations, and optionally deducing therefrom information relating to at least one effect of the treatment.

By way of example, the treatment may comprise applying a cosmetic or a skin-care product, or it may comprise taking food supplements or medication.

In another of its aspects, the invention also provides a method of predicting changes that will occur in a physical or biological parameter of some tissue, e.g. the size of its corneocytes, its apparent age, . . . , the method comprising:
  making at least one observation by implementing the method as defined above; and
  from the result of the observation, predicting changes that will occur in said parameter.

In another of its aspects, the invention also provides a method of prescribing a substance, for example a cosmetic substance, the method comprising:
  making at least one observation by implementing the method as defined above; and
  from the result of the observation, prescribing at least one substance, for example one cosmetic substance.

In another of its aspects, the invention also provides a method of observing biological tissue, the method comprising:
  putting a first end of the fibers of a bundle of optical fibers into contact with a surface of the tissue, to observe an image at a second end of the fibers of the bundle.

In another of its aspects, the invention also provides a method of observing corneocytes comprising:
  illuminating at a first wavelength skin,
  observing an image of the corneocytes at a second wavelength different form the first, using a bundle of optical fibers, the image being observed at a second end of the bundle while the first end receives light from the skin.

The skin illumination may be obtained by injecting light into the second end of the bundle or otherwise.

In another of its aspects, the invention also provides a method of observing a surface of the tissue through an optical system assembled to a first end of a bundle of optical fibers so as to produce at a second end thereof an image.

The image may be observed through a lens, for example a microscope lens.

Light may be injected in the second end of the bundle to illuminate the surface of the tissue.

In another of its aspects, the invention also provides skin-imaging apparatus comprising:
  a bundle of optical fibers having a first end for collecting light from a surface of a tissue;
  an injector system for injecting light into the bundle at a second end thereof; and
  an analyzer system for analyzing an image formed at the second end of the bundle.

Advantageously, the apparatus further comprises:
  an image-processor system configured to deliver at least one information associated with the observed corneocytes.

Advantageously, the apparatus further comprises an image-processor system configured to deliver at least one information associated with the observed corneocytes, e.g. relating to the number of corneocytes present in the image and/or to their mean or median size.

The processor system may be arranged to deliver information automatically.

The resolution of said bundle may be sufficient for allowing the obtained image to show corneocytes present at the surface of the skin.

The first end of the bundle may be configured for contacting skin.

The first end of the bundle may be configured for observing skin while being spaced from the surface of the tissue by a distance.

The apparatus may further comprises an optical system comprising at least one lens.

The at least one lens may comprise at least one of a magnifying lens and a collimating lens.

The optical system may comprise a first lens and second lens.

The first lens may be a collimating lens and the second lens may be a magnifying lens, light from the surface of the tissue passing through the second lens and then the first lens.

The length of the first lens may range from 4.4 to 6.8 mm and the length of the second lens may range from 1.8 to 2.9 mm.

The at least one lens of the optical system may comprise a lens with an index gradient, the g value of the index gradient at 670 nm may be greater or equal to 0.25 mm-1. The distance from which the optical system is spaced from the surface of the tissue during observation may range from 100 μm to 1 mm, for example from 200 μm to 500 μm.

The apparatus may include a dichroic mirror, a light source, and a camera, the dichroic mirror reflecting, into the bundle of fibers, the light emitted by the light source, and the camera observing the image that is reflected back via the fibers, after passing through the dichroic mirror.

The apparatus may include a monochromatic filter or a monochromator associated with the light source. The apparatus may also include a monochromatic filter or a monochromator associated with the camera.

The invention is not limited to a particular light source, and said light source may comprise an incandescent lamp, a light emitting diode (LED), a laser, or a discharge lamp (xenon, mercury, . . . ).

The apparatus may include a recorder system enabling images to be stored. By way of example, this can enable them to be compared with other images coming from the same person or from a reference population, for example.

The relative positions of the fibers within the bundle may be the same at the inlet and at the outlet of said bundle.

In another of its aspects, the invention also provides a kit comprising:
  apparatus as defined above; and
  a receptacle containing a fluorescent marker for applying to the skin before it is observed.

The invention also provides a method of promoting a treatment and/or the sale of a substance, which method puts forward an effect of the substance, as revealed by an observation method as defined above. The promotion could be carried out using any sales channel.

The invention can be better understood on reading the following detailed description of non-limiting embodiments thereof, and on examining the accompanying drawings, in which.

Figure 1:
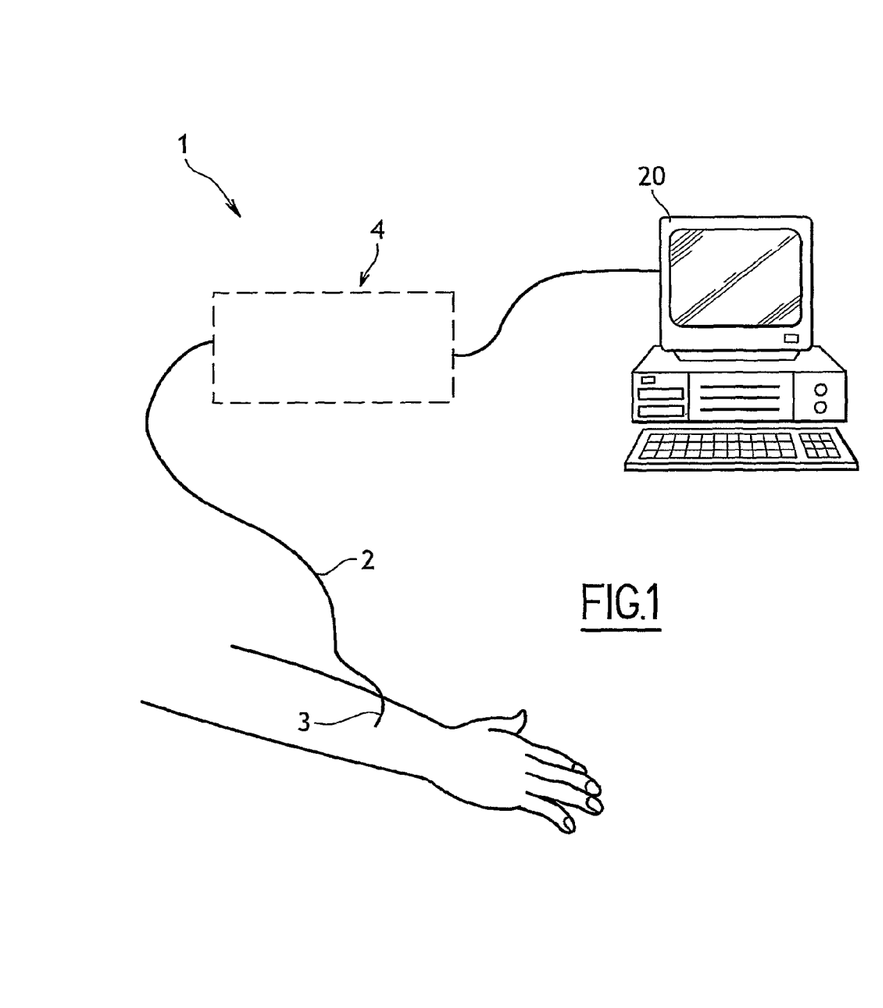
FIG. 1 is a diagrammatic view of imaging apparatus according to an exemplary embodiment of the invention.

FIG. 1 shows apparatus 1 in accordance with the invention and including a bundle 2 of optical fibers having a first end 3 that may for example be put directly into contact with an observed surface, e.g. a skin surface, as shown, without any need for intermediate optics.

The other end 5 of the bundle 2 is connected to a device 4 which is described in greater detail below, with reference to FIG. 3.

Figures 2, 3:
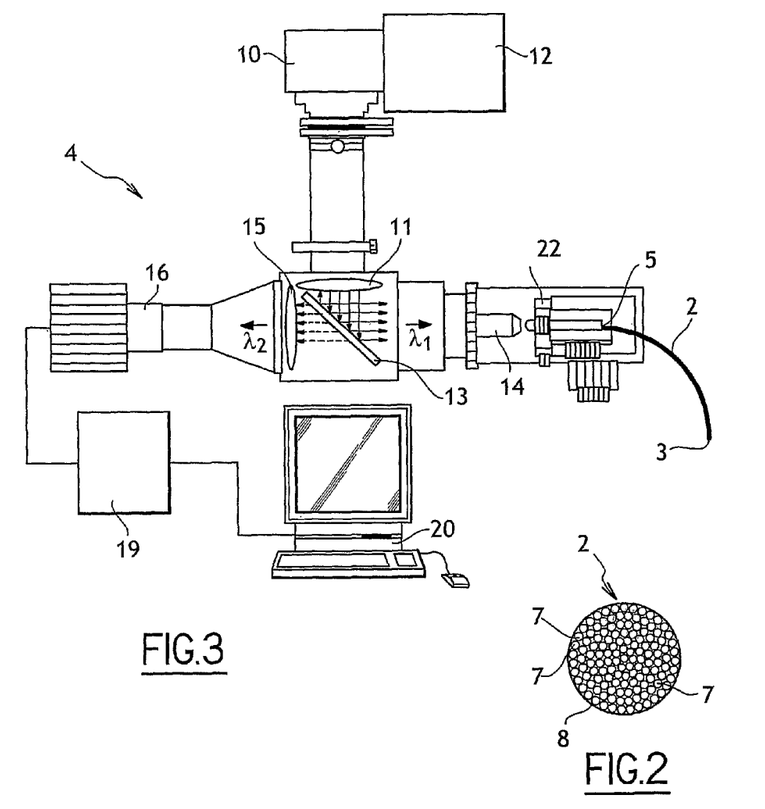
FIG. 2 is a diagrammatic and fragmentary cross-section of the bundle of optical fibers in FIG. 1.
FIG. 3 is a diagrammatic view showing the arrangement of various optical components of the FIG. 1 apparatus.

The optical fibers 7 of the bundle 2 extend parallel to one another, and may be of circular cross-section, as shown in FIG. 2. The fibers 7 may be contained in a sheath 8 which may also be of circular section.

In the embodiment under consideration, the disposition of the fibers 7 relative to one another at the inlet of the bundle is the same as their relative disposition at the outlet of the bundle, with each fiber thus constituting a kind of pixel in the image.

In the embodiment under consideration, the fibers 7 are substantially identical, e.g. being made of glass, and being of diameter that is less than or equal to 4 µm, with the number of fibers 7 being greater than or equal to 10,000, for example, and with the total section occupied by the fibers 7 of the bundle being greater than 0.5 mm², for example. For the purposes of clarity, the drawing shows only some of the fibers, without complying with relative proportions.

The size and the number of fibers can be selected as a function of the desired resolution.

As can be seen in FIG. 3, the device 4 comprises a light source 10, e.g. an incandescent lamp or a discharge lamp and its power supply 12, a first monochromatic filter 11 enabling the light emitted by the source 10 to be filtered around a first wavelength $\lambda_1$, and a dichroic mirror 13 enabling a fraction of the light coming from the filter 11 to be reflected towards a lens 14 that is arranged to inject the light into the second end 5 of the bundle 2. The lens 14 may be a microscope lens.

The apparatus 1 may comprise a micro-positioner 22 to facilitate placing the bundle 2 substantially in front of the lens 14.

Part of the light that is reflected back into the bundle 2 at the first end 3 passes through the dichroic mirror 13, and then through a second optical filter 15 centered on a second wavelength $\lambda_2$ that is different from the first, so as to be observed by an image-analyzer system including an array sensor 16, e.g. a CCD sensor and a CCD controller 19 sending data to an image processor system 20. By way of example, the image-analyzer system is a digital camera.

In a variant, the filters 11 and 15 are replaced by monochromators.

In the embodiment under consideration, the dichroic mirror 13 presents a plane that is at an angle of substantially 45° to the incident light emitted by the source 10, and the light that is returned by the lens 14 is along a direction that is substantially perpendicular to the light emitted by the source 10.

Naturally, various modifications can be applied to the device 4 without going beyond the ambit of the present invention.

For example, the source 10 that is used can be substantially monochromatic, e.g. by using LEDs or a laser. Where appropriate, the sensor 16 can be wavelength selective, and not require the presence of the second filter 15. When the source 10 is monochromatic, the first filter 11 can be eliminated.

In the exemplary embodiment of FIG. 1, the first end of the bundle may be put directly into contact with a surface to be observed.

Figure 11:
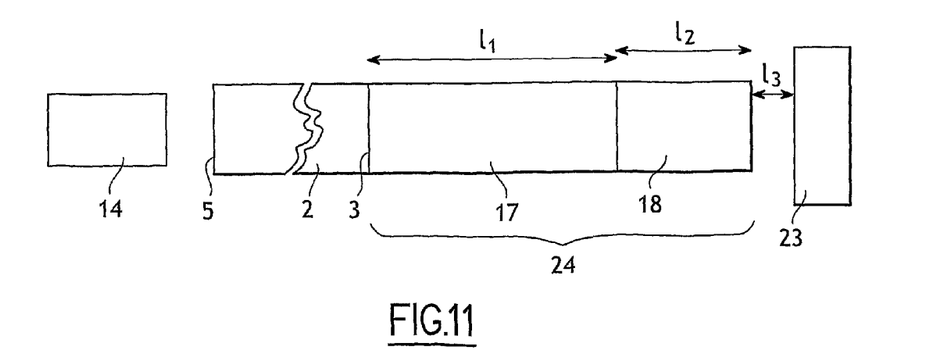
FIG. 11 shows the possibility of adding to the apparatus of FIG. 3 an optical system.

However, it is also possible, according to another exemplary embodiment, to observe the surface of the tissue at a distance though an optical system 24 assembled to the first end of the bundle 2 of fibers, as shown in FIG. 11. The device 4 may be as described above. The optical system 24 may be spaced from the surface of the tissue 23 during observation by a distance $l_3$, for example about 300 µm.

In the embodiment of FIG. 11, the optical system 24 is fixed to the bundle 2, with a glue transparent to visible light, but the optical system 24 may be fixed differently for example using an external sleeve.

The optical system 24 may comprise a proximal or first lens 17 and a distal or second lens 18.

The first lens 17 may be a collimating lens and the second lens 18 may be a magnifying lens. The first lens 17 may collimate the light beam outing from the bundle and the second lens 18 may re-focus the light beam towards the surface to be observed.

The lenses 17 and 18 may be cylindrical.

In an exemplary embodiment, the characteristics of the first lens may be:
numerical aperture=0.2
pitch=0.25
central refractive index at 670 nm=1.5297
g value of the index gradient at 670 nm=0.255 mm$^{-1}$
external diameter=1 mm
length $l_1$=5.5 mm The characteristics of the second lens may be:
numerical aperture=0.5
pitch=0.2
central refractive index at 670 nm=1.6289
g value of the index gradient at 670 nm=0.654 mm$^{-1}$
external diameter=1 mm
length $l_2$=2.3 mm With such an optical system, the spatial resolution may improve by a 2.7 factor, from 3 µm to 1.1 µm.

The image processor system 20 may be in the form of a micro-computer.

The micro-computer can be programmed to analyze at least one image observed by the array sensor 16.

Figure 5:
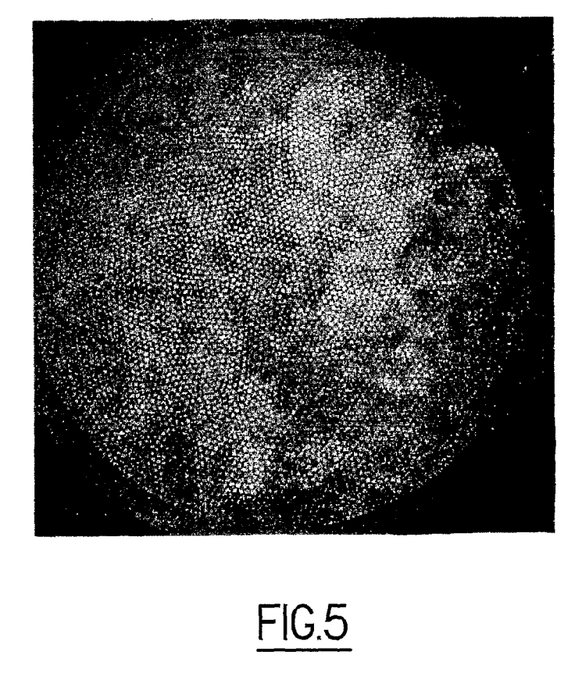
FIG. 5 is an example of an image that can be observed using the FIG. 1 apparatus.

When the observed surface is a human skin surface, the image observed by the array sensor 16 can be in the form shown in FIG. 5, for example, in which the outlines of the corneocytes present at the surface of the skin can be seen.

The image-processor system 20 can be arranged to calculate a mean or median size of corneocytes either from a single image or from a plurality of images and by performing statistical processing thereon, with the various images being observed after moving the end 3 over the skin, for example.

Figures 6, 7:
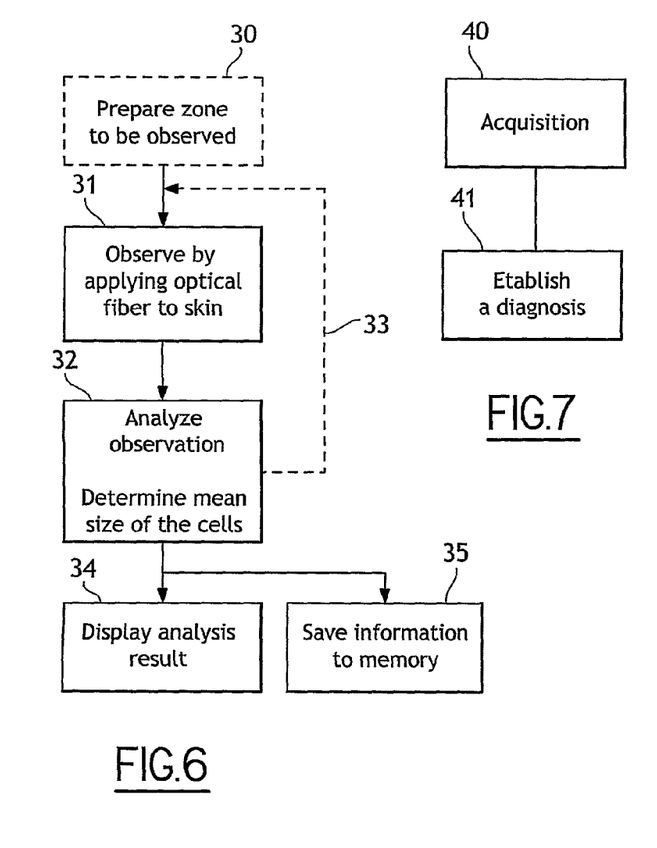
FIGS. 6 to 10 are block diagrams showing examples of methods of the invention.

As shown in FIG. 6, the apparatus 1 can be used as follows:

In a first step 30, the observed surface can be prepared for observation.

For human skin, preparation can comprise applying a fluorescent marker to the skin, e.g. a solution of fluorescein or fluorescein sodium.

The skin receiving light at the wavelength $\lambda_1$ can re-emit light at a wavelength $\lambda_2$ because of the presence of the fluorescent marker whose concentration varies as a function of the disposition of the cells, and in particular causes the outlines of said cells to appear. For fluorescein, the wavelength that is absorbed is about 493.5 nanometers (nm), so $\lambda_1$ is set to be close to that value. The wavelength that is emitted is about 520 nm, and $\lambda_2$ is selected to be close to that value.

Then, the end 3 of the bundle 2 can be applied to in the absence of the optical system 24 or placed in the vicinity of the skin in the presence of the optical system 24, and the corresponding image is observed in a step 31. The image can be analyzed in a step 32 by the micro-computer, so as to determine the mean size of the corneocytes, as explained above. In order to determine the mean size, it is possible to determine the number of corneocytes present in the observation field, for example.

Where appropriate, a plurality of images resulting from moving the end 3 and/or the micropositioner 22 can be analyzed in succession, as shown by arrow 33.

The result of the analysis, e.g. a mean size for the corneocytes, can be displayed in a step 34, with at least some of the corresponding information being saved to memory, where appropriate, e.g. the mean size.

Naturally, it is not beyond the ambit of the present invention for the device 4 and the processor system 20 not to form two distinct entities, but rather a single, common entity, the device 4 then being equipped with a keyboard and with a screen, for example.

The invention may make it possible to obtain a mean size for the corneocytes, and this can be useful, e.g. in order to perform a diagnosis, as shown in FIG. 7. In this event, the method may include a first step 40 of acquiring one or more images of the surface of the skin, and a step 41 of establishing a diagnosis from information supplied by the apparatus of the invention, e.g. a mean or median size for the corneocytes.

Where appropriate, the information associated with the corneocytes can be combined with other information relating to the person that is the subject of the study.

By way of example, the diagnosis can relate to aging of the skin. By way of example, it is thus possible to inform the person of their position relative to a reference population, e.g. a population within the same age group.

By way of example, it is possible to give the person a score as a function of that person's degree of aging relative to the reference population. It is also possible to propose a treatment, e.g. applying a substance to retard aging of the skin.

The diagnosis may also relate to a pathology of the skin.

Figure 8:
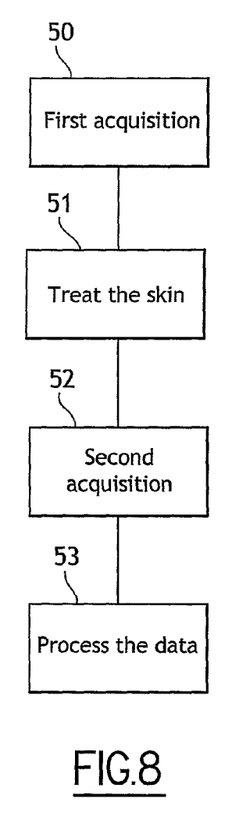

The invention may also be used to reveal the effect of a treatment on the skin, as shown in FIG. 8.

In this method, in a first step 50, one or more images can be acquired of a skin surface, so as to determine first information associated with the size of the corneocytes that are present, then in a step 51, the skin is treated, and after treatment, in a step 52, one or more images are again acquired of the now treated region.

The images and/or the information corresponding to steps 50 and 52 may be compared in a step 53, so as to reveal, for example, a change that has occurred in the mean or medium size of the corneocytes, and the effect of the treatment.

By way of example, such a method may make it possible to quantify the activity of an agent, or to reveal an action of an agent during treatment.

Figure 9:
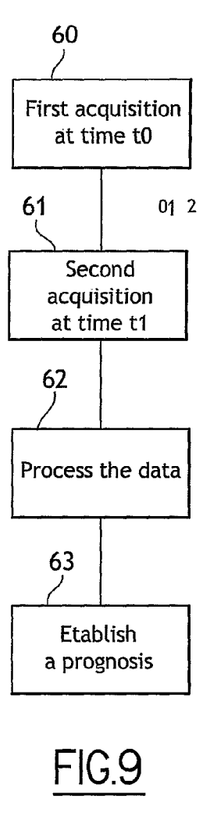

As shown in FIG. 9, the invention may also be used in a method in which one or more images are acquired in first and second steps 60 and 61 that are successive over time.

In a step 62, the data is then processed as a function of the changes that have occurred in at least one parameter associated with the images, so as to establish a prognosis in a step 63. The prognosis may determine the rate at which the mean size of the corneocytes is changing, so as to predict a subsequent state of aging of the skin. By way of example, the user can be informed of the expected state of the skin at different ages. As a function of the prognosis carried out, one or more substances or treatments can be recommended, where appropriate.

Figure 10:
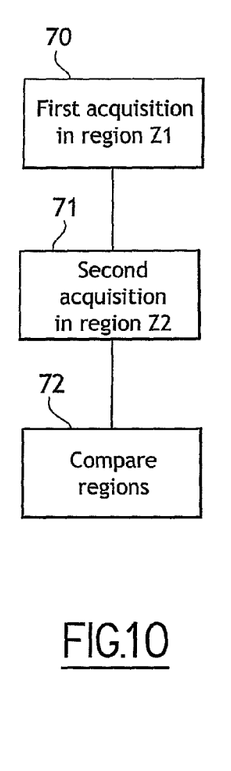

As shown in FIG. 10, the invention may also be useful in a method in which two acquisitions are carried out in steps 70 and 71 on different regions $Z_1$ and $Z_2$ of the skin, e.g. regions exposed in different ways to a treatment or to an environment, and in a step 72, at least some of the information associated with the corresponding images is compared.

By way of example, such a method makes it possible to reveal the effect of a particular environment on the skin, e.g. the effect of exposure to ultraviolet radiation on photo-aging of the skin.

Naturally, the invention is not limited to the embodiments described above.

For example, the invention may apply to reconstructed skin, for example.

Figure 4:
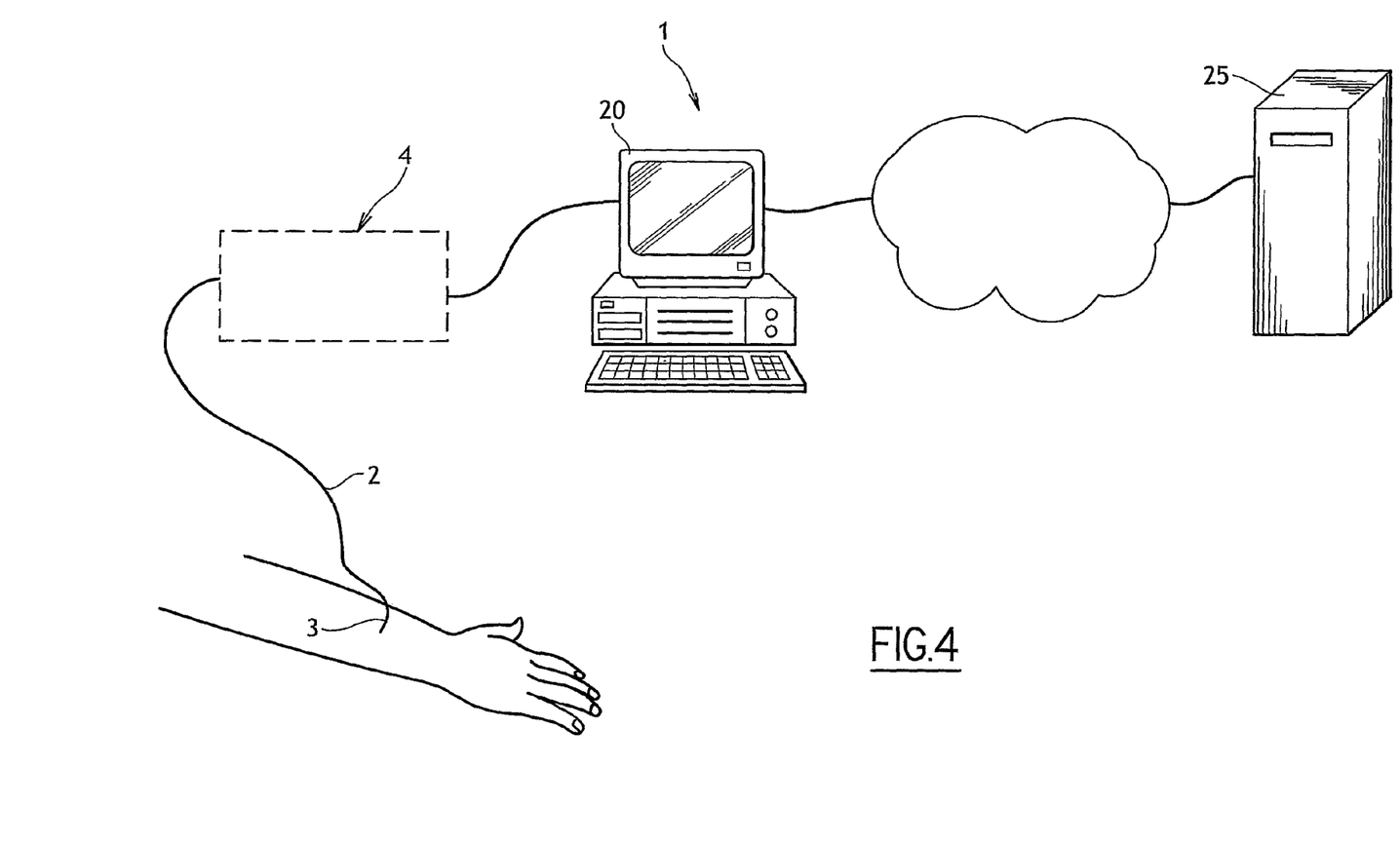
FIG. 4 shows the possibility of connecting the FIG. 1 apparatus to a remote server.

The surface observed using the end 3 of the optical-fiber bundle 2 can be the outside surface of the dermis, or even the inside surface of a hair follicle, e.g. when the size of the bundle 2 makes that possible.

Where appropriate, the image-processor system can be remote, as shown in FIG. 4. By way of example, the micro-computer shown in FIG. 3 can be connected via a computer and/or telephone network to a server 25 at a processing center, which server sends back information relating, for example, to the size of the corneocytes and/or to a diagnosis, and where appropriate, advice relating to the purchase of a cosmetic. By way of example, the server 25 may be arranged to send information to a goods-shipping center, in order to send a diagnosis accompanied by a cosmetic directly to a consumer. The server 25 may also send information relating to the result of a treatment.

The processor system 20 may also be integrated in the device 4.

The invention can find applications other than in the field of cosmetics, given that certain pathologies of the epidermis affect the size of the corneocytes, e.g. reducing their size in the case of psoriasis.

The invention may also apply to observing keratinous fibers such as hair, for example.

Throughout the description, including in the claims, the expression "comprising a" should be understood as being synonymous with "comprising at least one" unless specified to the contrary.

The invention claimed is:

1. A method of observing biological tissue being skin or keratinous fiber, the method comprising:
   (a) injecting light centered on a first wavelength ($\lambda_1$) into a second end portion of a fiber bundle such that the light travels through fibers of the fiber bundle and illuminates a surface of the tissue near a first end portion of the fiber bundle;

(b) collecting reflected light from the surface of the tissue with the first end portion of the fiber bundle such that the reflected light travels back via the fibers to the second end portion of the fiber bundle; and (c) observing at least one image of the tissue produced by reflected light emanating from the second end portion of the bundle at a second wavelength ($\lambda_2$) that is different from the first wavelength, wherein the at least one image is processed so as to determine information associated with corneocytes and wherein each fiber corresponds to one pixel of the image.

2. A method according to claim 1, wherein the first end of the bundle is put into contact with the surface of the tissue.

3. A method according to claim 1, wherein the first end of the bundle is spaced from the surface of the tissue by a distance.

4. A method according to claim 3, wherein light is collected by the first end of the bundle through an optical system comprising at least one lens.

5. A method according to claim 4, wherein the distance between the optical system and the surface of the tissue ranges from 100 µm to 1 mm.

6. A method according to claim 5, wherein the distance between the optical system and the surface of the tissue ranges from 200 µm to 500 µm.

7. A method according to claim 3, wherein the spatial resolution is better than 1.5 µm.

8. A method according to claim 4, wherein the at least one lens comprises a magnifying lens.

9. A method according to claim 8, wherein the at least one lens comprises a collimating lens.

10. A method according to claim 4, wherein the optical system comprises a first lens and second lens, light from the surface of the tissue passing through the second lens and then the first lens.

11. A method according to claim 10, wherein the first lens is a collimating lens and the second lens is a magnifying lens.

12. A method according to claim 10, wherein the length of the first lens ranges from 4.4 to 6.8 mm.

13. A method according to claim 10, wherein the length of the second lens ranges from 1.8 to 2.9 mm.

14. A method according to claim 4, wherein the at least one lens comprises a lens with an index gradient.

15. A method according to claim 14, wherein the at least one lens with an index gradient has a g value of the index gradient at 670 nm greater or equal to 0.25 mm-1.

16. A method according to claim 4, wherein the at least one lens is cylindrical.

17. A method according to claim 16, wherein the at least one lens has an external diameter less than or equal to 2 mm.

18. A method according to claim 1, wherein the spatial resolution of the bundle is better than 5 µm.

19. A method according to claim 1, wherein the spatial resolution is better than 4 µm.

20. A method according to claim 1, wherein the spatial resolution is better than 3 µm.

21. A method according to claim 1, wherein the optical fibers have a diameter that is less than or equal to 4 µm.

22. A method according to claim 21, wherein the diameter lies in the range from about 2 µm to about 3 µm.

23. A method according to claim 1, wherein the bundle comprises not less than 2500 optical fibers.

24. A method according to claim 23, wherein the bundle comprises not less than 10,000 optical fibers.

25. A method according to claim 1, wherein a section occupied by the bundle of optical fibers is greater than or equal to 0.01 mm$^2$.

26. A method according to claim 25, wherein the section is greater or equal to 0.1 mm$^2$.

27. A method according to claim 1, wherein the observation is made as an in vivo observation.

28. A method according to claim 1, wherein the observation is made as an in vitro observation.

29. A method according to claim 1, wherein the information relates to the number of corneocytes present in the at least one image.

30. A method according to claim 1, wherein the information relates to the mean or median size of the corneocytes.

31. A method according to claim 1, wherein prior to making the observation, a fluorescent marker is put into contact with the tissue.

32. A method according to claim 1, wherein the wavelengths are selected as a function of a fluorescent marker put into contact with the tissue so as to maximize contrast in the obtained image.

33. A method according to claim 1, wherein the at least one image is acquired with an array sensor.

34. A method according to claim 33, wherein the array sensor is a CCD sensor.

35. A method according to claim 1, wherein at least two observations are made at two different locations of the tissue.

36. A method according to claim 35, wherein two observations are made at two respective regions of the tissue that have been exposed in different ways to a given environment.

37. A method according to claim 36, wherein the two regions have been exposed in different ways to ultraviolet light.

38. A method according to claim 35, wherein the two regions have been treated differently with a substance.

39. A method according to claim 1, wherein information relating to aging of the skin is delivered.

40. A method according to claim 1, wherein the surface of the tissue is situated inside a hair follicle.

41. A method according to claim 1, wherein the result of an observation is compared with reference data.

42. A method according to claim 1, wherein a plurality of observations are made at different locations, and wherein the results of the various observations are processed statistically to obtain a value that is representative of an observed parameter.

43. A method according to claim 42, wherein the value is a mean or median value.

44. A method of revealing the effect of a treatment, the method comprising:
    before the treatment, making a first observation by means of the method as defined in claim 1;
    after the treatment, making a second observation by means of the method as defined in claim 1; and
    comparing the results of the first and second observations.

45. A method according to claim 44, wherein information relating to at least one effect of the treatment is determined as a function of the comparison of the results of the first and second observations.

46. A method of predicting changes that will occur in at least one physical and/or biological parameter of some tissue, the method comprising:
    making at least one observation by implementing the method as defined in claim 1; and
    from the result of the observation, predicting changes that will occur in said parameter.

47. A method of prescribing a cosmetic, the method comprising:
   making at least one observation by implementing the method as defined in claim 1; and
   from the result of the observation, prescribing at least one cosmetic.

48. A method according to claim 1, wherein:
   the light is injected with an injector system, and
   the observing at least one image of the tissue at a second end of the bundle comprises analyzing the image with an analyzer system.

49. Skin-imaging apparatus comprising:
   a bundle of optical fibers having a first end for collecting light from a surface of a tissue;
   an injector system for injecting light into the bundle at a second end of the bundle; and
   an analyzer system for analyzing an image formed at the second end of the bundle,
   an image-processor system configured to deliver at least one piece of information associated with corneocytes that are observed by the skin-imaging apparatus,
   a dichroic mirror,
   a light source,
   a camera,
   a monochromatic filter or a monochromator associated with the light source,
   a monochromatic filter or a monochromator associated with the camera,
   the dichroic mirror reflecting, into the bundle of fibers, a fraction of the light emitted by the light source, and the camera being configured to observe the image that is reflected back via the fibers, after passing through the dichroic mirror,
   wherein each fiber corresponds to one pixel of the image.

50. Apparatus according to claim 49, wherein the resolution of said bundle is sufficient for allowing observation of corneocytes at the surface of the skin.

51. Apparatus according to claim 49, wherein the first end of the bundle is configured for contacting skin.

52. Apparatus according to claim 49, wherein the first end of the bundle is configured for observing skin while being spaced from the surface of the tissue by a distance.

53. Apparatus according to claim 49, further comprising an optical system comprising at least one lens.

54. Apparatus according to claim 52, wherein a distance between the optical system and the surface of the tissue ranges from 100 μm to 1 mm.

55. Apparatus according to claim 53, wherein the at least one lens comprises a magnifying lens.

56. Apparatus according to claim 55, wherein the at least one lens comprises a collimating lens.

57. Apparatus according to of claim 53, wherein the optical system comprises a first lens and second lens, light from the surface of the tissue passing through the second lens and then the first lens.

58. Apparatus according to of claim 53, wherein the first lens is a collimating lens and the second lens is a magnifying lens.

59. Apparatus according to claim 53, wherein the length of the first lens ranges from 4.4 to 6.8 mm.

60. Apparatus according to claim 53, wherein the length of the second lens ranges from 1.8 to 2.9 mm.

61. Apparatus according to claim 53, wherein the at least one lens comprises a lens with an index gradient.

62. Apparatus according to claim 61, wherein the at least one lens with an index gradient has a g value of the index gradient at 670 nm greater or equal to 0.25 mm$^{-1}$.

63. Apparatus according to claim 53, wherein the at least one lens is cylindrical.

64. Apparatus according to claim 63, wherein the at least one lens has an external diameter less than or equal to 2 mm.

65. Apparatus according to claim 53, further including a recorder system enabling images to be stored.

66. Apparatus according to claim 53, wherein the fibers at the inlet and at the outlet of the bundle have identical positions relative to one another.

67. A kit comprising:
   apparatus as defined in claim 53 and
   a receptacle containing a fluorescent marker for applying to the skin before it is observed.

* * * * *